United States Patent
Gobron

(10) Patent No.: US 12,163,154 B2
(45) Date of Patent: Dec. 10, 2024

(54) USE OF PEPTIDE COMPOUNDS FOR PROMOTING SURVIVAL, GROWTH AND CELL DIFFERENTIATION

(71) Applicant: Axoltis Pharma, Clermont-Ferrand (FR)

(72) Inventor: Stéphane Gobron, Dallet (FR)

(73) Assignee: Axoltis Pharma, Clermont-Ferrand (FR)

( * ) Notice: Subject to any disclaimer, the term of this patent is extended or adjusted under 35 U.S.C. 154(b) by 1259 days.

(21) Appl. No.: 16/466,177

(22) PCT Filed: Dec. 5, 2017

(86) PCT No.: PCT/EP2017/081562
§ 371 (c)(1),
(2) Date: Jun. 3, 2019

(87) PCT Pub. No.: WO2018/104325
PCT Pub. Date: Jun. 14, 2018

(65) Prior Publication Data
US 2020/0080053 A1 Mar. 12, 2020

(30) Foreign Application Priority Data
Dec. 5, 2016 (EP) .................................... 16202294

(51) Int. Cl.
*C12N 5/0793* (2010.01)
*C07K 7/06* (2006.01)
*C07K 14/78* (2006.01)

(52) U.S. Cl.
CPC .............. *C12N 5/0619* (2013.01); *C07K 7/06* (2013.01); *C07K 14/78* (2013.01); *C12N 2501/115* (2013.01); *C12N 2501/998* (2013.01); *C12N 2506/02* (2013.01); *C12N 2506/1353* (2013.01)

(58) Field of Classification Search
CPC ............ C12N 5/0619; C12N 2501/115; C12N 2501/998; C12N 2506/02; C12N 2506/1353; C12N 2533/50; C07K 7/06; C07K 14/78; C07K 7/04
See application file for complete search history.

(56) References Cited

U.S. PATENT DOCUMENTS

| | | | |
|---|---|---|---|
| 5,181,457 A | 1/1993 | Toshiyuki | |
| 6,995,140 B1 | 2/2006 | Meiniel et al. | |
| 10,501,497 B2 | 12/2019 | Bridon et al. | |
| 2010/0316613 A1* | 12/2010 | Upton ................. | C12N 5/0606 435/405 |
| 2011/0178023 A1 | 7/2011 | Meiniel et al. | |
| 2017/0246247 A1 | 8/2017 | Meiniel et al. | |
| 2018/0265549 A1 | 9/2018 | Bridon et al. | |
| 2020/0080053 A1 | 3/2020 | Gobron | |

FOREIGN PATENT DOCUMENTS

| | | |
|---|---|---|
| CN | 101215545 | 7/2008 |
| CN | 101451123 | 6/2009 |
| CN | 101831401 | 9/2010 |
| EP | 0 478 101 | 4/1992 |
| JP | A-2001-510034 | 7/2001 |
| JP | 2020-504094 | 2/2020 |
| WO | WO2003047526 A2 * | 11/2003 |
| WO | WO 2008/090285 | 11/2009 |
| WO | WO-2016016593 | 2/2016 |

OTHER PUBLICATIONS

Lindke et al. "Regulating the availability of transforming growth factor ß1 in B104 neuroblastoma cells." Exp Neurol. Sep. 2010;225(1):123-32. (Year: 2010).*
Ye et al. "Induction of human bone marrow mesenchymal stem cells differentiation into neural-like cells using cerebrospinal fluid." Cell Biochem Biophys. Apr. 2011;59(3):179-84. (Year: 2011).*
Mu et al. "Comparative study of neural differentiation of bone marrow mesenchymal stem cells by different induction methods." Genet Mol Res. Oct. 30, 2015;14(4):14169-76. (Year: 2015).*
Agarawal et al. "Pluripotent and Multipotent Stem Cells Display Distinct Hypoxic miRNA Expression Profiles." PLoS One. Oct. 26, 2016;11(10):e0164976. (Year: 2016).*
Ebeid et al. "Transcriptome-wide comparison of the impact of Atoh1 and miR-183 family on pluripotent stem cells and multipotent otic progenitor cells." PLoS One. 2017; 12(7): e0180855. (Year: 2017).*
Le Douce et al. "Subcommissural Organ-Spondin-Derived Peptide Restores Memory in a Mouse Model of Alzheimer's Disease." Front Neurosci. 2021; 15: 651094. (Year: 2021).*
Gobron et al. "Subcommissural organ/Reissner's fiber complex: Characterization of SCO-spondin, a glycoprotein with potent activity on neurite outgrowth." Glia. Nov. 2000;32(2):177-91. (Year: 2000).*
Young et al. "Human Pluripotent and Progenitor Cells Display Cell Surface Cluster Differentiation Markers CD10, CD13, CD56, and MHC Class—I." Proceedings of the society for experimental biology and medicine 221.1 (1999): 63-72. (Year: 1999).*
Macnicol et al. "Function and regulation of the mammalian Musashi mRNA translational regulator." Biochem Soc Trans. Jun. 2008; 36(Pt 3): 528-530. (Year: 2008).*
Miyazaki et al. "Efficient Adhesion Culture of Human Pluripotent Stem Cells Using Laminin Fragments in an Uncoated Manner."Sci Rep.Jan. 30, 2017:7:41165. (Year: 2017).*
Liu et al. "The Regenerative Potential of bFGF in Dental Pulp Repair and Regeneration." Front Pharmacol. 2021; 12: 680209. Published online Jul. 20, 2021 (Year: 2021).*
Guerra, et al, Understanding How the Subcommissural Organ and Other Periventricular Secretory Structures Contribute via the Cerebrospinal Fluid to Neurogenesis, Dec. 23, 2015, pp. 1-18, Frontiers in Cellular Neuroscience.

(Continued)

*Primary Examiner* — Titilayo Moloye
(74) *Attorney, Agent, or Firm* — B. Aaron Schulman, Esq.; Stites & Harbison, PLLC

(57) ABSTRACT

The present invention relates to the use of peptide compounds for promoting survival and/or growth and/or differentiation of progenitor cells or stem cells.

2 Claims, 6 Drawing Sheets
Specification includes a Sequence Listing.

(56) References Cited

OTHER PUBLICATIONS

Sakka L et al: "SCO-spondin derived peptide NX210 induces neuroprotection in vitro and promotes fiber regrowth and functional recovery after spinal cord injury", PLOS ONE, Public Li Bra Ry of Science, US, vol. 9, No. 3, Mar. 25, 2014 (Mar. 25, 2014), pp. e93179-1, XP002734572, ISSN: 1932-6203, DOI: 10.1371/JOURNAL. PONE.0093179 [retrieved on Jan. 1, 2014] the whole document.

Okabe et al: "Development of neuronal precursor cells and functional postmitotic neurons from embryonic stem cells in vitro", Mechanisms of Development, Elsevier Science Ireland Ltd, IE, vol. 59, No. 1, Sep. 1, 1996 (Sep. 1, 1996), pp. 89-102, XP005788754, ISSN: 0925-4773, DOI: 10.1016/0925-4773(96)00572-2 cited in the application the whole document figure 2.

A. Vera et al: "SCO-spondin from embryonic cerebrospinal fluid is required for neurogenesis during early brain development", Frontiers in Cellular Neuroscience, vol. 7, Jan. 1, 2013 (Jan. 1, 2013), XP055357209, DOI: 10.3389/fncel.2013.00080 abstract p. 2, left-hand column, paragraph 1-3; figure 8 p. 12, right-hand column, paragraph 2.

Elsa Abranches et al: "Neural Differentiation of Embryonic Stem Cells In Vitro: A Road Map to Neurogenesis in the Embryo", PLOS ONE, vol. 4, No. 7, Jul. 21, 2009 (Jul. 21, 2009), p. e6286, XP055357199, DOI: 10.1371/journal.pone.0006286 abstract p. 2, left-hand column, paragraph 3.

International Search Report for PCT/EP2017/081562, dated Feb. 22, 2018.

Written Opinion of the International Searching Authority for PCT/EP2017/081562, dated Feb. 22, 2018.

Gobron, et al, "Subcommissural Organ/Reissner's Fiber Complex: Characterization of SCO-Spondin, a Glycoprotein With Potent Activity on Neurite Outgrowth", 2000, vol. 32, pp. 177-191, GLIA.

Meiniel, et al, "SCO-Spondin, a Glycoprotein of the Subcommissural Organ/Reissner's Fiber Complex: Evidence of a Potent Activity on Neuronal Development in Primary Cell Cultures", 2001, pp. 484-495, vol. 52, Microscopy Research and Technique.

El-Bitar, et al, "Effects of SCO-spondin thrombospondin type 1 repeats (TSR) in comparison to Reissner's fiber material on the differentiation of the B104 neuroblastoma cell line", 2001, pp. 361-369, vol. 304, Cell Tissue Res.

Cebrian et al, "Synthesis and biological activity of thrombospondin related peptides", pp. 81-89, 2001, vol. 4, Current Topics in Peptide & Protein Research.

Monnerie, et al, "Effects of synthetic peptides derived from SCO-spondin conserved domains on chick cortical and spinal-cord neuron in cell cultures", 1998, pp. 407-418, vol. 293, Cell Tissue Res.

Meiniel, et al, "The Thrombospondin Type 1 Repeat (TSR) and Neuronal Differentiation: Roles of SCO-Spondin Oligopeptides on Neuronal Cell Types and Cell Lines", 2003, pp. 1-39, vol. 230, International Review of Cytology.

Trivedi, et al, "The role of thiols and disulfides in protein chemical and physical stability", Dec. 2009, pp. 614-625, vol. 10, No. 6, Curr Protein Pept Sci.

Japanese Office Action for corresponding Application JP 2019-530185 dated Oct. 25, 2021.

* cited by examiner

A. Patient n°1

B. Patient n°2

USE OF PEPTIDE COMPOUNDS FOR PROMOTING SURVIVAL, GROWTH AND CELL DIFFERENTIATION

The present invention relates to the use of peptide compounds for promoting survival and/or growth and/or differentiation of progenitor cells or stem cells.

Due to the increasing life expectancy, neurological disorders and neurodegenerative diseases constitute an increasing socio-economic weight in western countries, more than any other disease. Various pharmacological approaches have been developed to treat these diseases but little success has been achieved and the search for new treatments continues actively. In this context, recent works on stem cells raise many hopes. In particular, stem cells are particularly attractive because they have two interesting abilities:
- an ability to self-renewal, that means they can multiply identically to obtain a large number of cells, and
- an ability to differentiate, that means they can provide mature adult cells ready to ensure a particular function, in particular neurons.

Thus, stem cells could be used to repair damages of the central nervous system. However, stem cells are rare and the development of clinical approaches based on these cells requires new protocols enabling expansion and/or differentiation in accordance with the therapeutic practice.

Some methods have been developed to multiply and differentiate stem cells using optimized culture media and/or using additive compounds such as growth factors. Some approaches have also been developed using the properties of the thrombospondins, a family of extracellular glycoproteins. These glycoproteins are involved in the modulation of the phenotypes during development and in various cellular functions such as cell-cell contact, cell adhesion, or communication between cells or between a cell and its environment.

In this context, the present invention provides the use of specific peptide compounds whose sequence is derived from a portion of TSR patterns (Thrombospondin type 1 repeat) present in the SCO-spondin, a specific glycoprotein of the central nervous system found in all vertebrates. This glycoproteins is a molecule of the extracellular matrix secreted by the subcommissural (SCO) organ in mammals. The SCO-spondin is a large protein of more than 4,500 amino acids with a multi-modular organization comprising various conserved patterns, in particular 26 TSR patterns in mammals.

TSR patterns are protein domains of about 55 residues, based on alignment of conserved amino acids cysteine, tryptophan and arginine. These patterns have been first identified in thrombospondin 1 (TSP-1), a molecule involved in coagulation. Then, they have been found in numerous molecules with various biological functions such as cell attachment, mobility, proliferation, cell aggregation, modulation of proteases or inhibition of angiogenesis.

In particular it has been shown that certain peptides derived from TSR patterns of the SCO-spondin exhibit biological activity on the nerve cells (WO 99/03890) and that these peptides act on nerve cells through a specific receptor (Bambad M. et al., Cell & Tissue Research, vol. 315, 15-25 (2004)). It has also been shown that such peptides promote the sprouting of neuritic extensions (WO 2008/090285).

However, there's a need for methods enabling expansion and/or differentiation of stem cells to obtain a specific type of cells, such as neurons.

The purpose of the invention is to provide peptide compounds and methods for promoting survival and/or growth and/or differentiation of progenitor cells or stem cells.

In a first aspect, the invention relates to the in vitro or ex vivo use of at least one peptide compound comprising or consisting in:

$$X_1\text{-}S\text{-}X_2\text{-}W\text{-}S\text{-}X_3\text{-}X_4\text{-}S\text{-}X_5,$$ (SEQ ID NO: 1)

wherein:
- $X_1$ is W or L-Nal2,
- $X_2$ is G, V, A, S or Abu,
- $X_3$ is S, D or A,
- $X_4$ is C* or Abu,
- $X_5$ is R—S, R—S-Nm, R—S—C*-G, R-Abu-Nm, R-Abu-C*-G, K-iPr-S-Nm or K-iPr-S—C*-G,
- Abu corresponds to a 2-aminobutyric acid residue,
- iPr corresponds to an isopropyl-lysine residue,
- Nal2 corresponds to a 2-naphthylalanine,
- Nm indicates that the COOH end has been replaced by a $NH_2$ end,
- * indicates that when both $X_4$ and $X_5$ represent or comprise a cysteine residue said cysteine residues can be linked by a disulfide bond, for promoting survival and/or growth and/or differentiation of progenitor cells or stem cells.

The invention is based on the unexpected observation made by the Inventors that these peptide compounds can stimulate the survival, the growth and the differentiation of progenitor cells or stem cells.

The expression "peptide compound" as used herein refers to a peptide, an oligopeptide, a polypeptide and a protein. This term also does not exclude post-expression modification of peptides. For example, peptides that include a disulfide bond or the covalent attachment of glycosyl groups, acetyl groups, lipid groups and the like are encompassed by the term "peptide compound".

The amino acids that form the peptide compounds of the invention can be natural or unnatural amino acids.

The expression "natural amino acids" refers to the L-form of amino acids that are found in natural proteins, namely: alanine (A), arginine (R), asparagine (N), acid aspartic acid (D), cysteine (C), glutamine (Q), glutamic acid (E), glycine (G), histidine (H), isoleucine (I), leucine (L), lysine (K), methionine (M), phenylalanine (F), proline (P), serine (S), threonine (T), tryptophan (W), tyrosine (Y) and valine (V).

The expression "unnatural amino acid" refers to the D-form of the natural amino acids, homo forms of certain natural amino acids (such as arginine, lysine, phenylalanine and serine), and nor forms of leucine and valine. It also includes synthetic amino acids such as alpha-aminobutyric acid (Abu), agmatine (Agm), alpha-arinoisobutyrique acid (Aib), N-formyl-Trp (F-trp), sarcosine, statine, ornithine, desaminotyrosine. The desaminotyrosine is incorporated at the N-terminus while agmatine and statine are incorporated at the C-terminus of these peptides.

In an embodiment, the invention relates to the in vitro or ex vivo use of at least one peptide compound comprising or consisting in:

$$X_1\text{-}S\text{-}X_2\text{-}W\text{-}S\text{-}X_3\text{-}X_4\text{-}S\text{-}X_5,$$ (SEQ ID NO: 1)

wherein:
X$_1$ is W or L-Nal2,
X$_2$ is G, V, A, S or Abu,
X$_3$ is S, D or A,
X$_4$ is C* or Abu,
X$_5$ is R—S, R—S-Nm, R—S—C*-G, R-Abu-Nm, R-Abu-C*-G, K-iPr-S-Nm or K-iPr-S—C*-G,
Abu corresponds to a 2-aminobutyric acid residue,
iPr corresponds to an isopropyl-lysine residue,
Nal2 corresponds to a 2-naphthylalanine,
Nm indicates that the COOH end has been replaced by a NH$_2$ end,
* indicates that when both X$_4$ and X$_5$ represent or comprise a cysteine residue said cysteine residues can be linked by a disulfide bond,
some specific amino acids can be replaced by their derivatives or analogs,
said peptide compound can be modified by amidation, by acylation, by PEGylation, by addition of amino acids in N-ter and/or in C-ter ends, by changes in staple peptides or by any conjugation method in particular with albumin, or polymers such as PEG, or a combination with gel or hydrogel,
said peptide can be cyclized,
for promoting survival and/or growth and/or differentiation of progenitor cells or stem cells.

In an embodiment, the invention relates to the in vitro or ex vivo use of at least one peptide compound comprising or consisting in:

$$X_1-S-X_2-W-S-X_3-X_4-S-X_5, \quad \text{(SEQ ID NO: 1)}$$

wherein:
X$_1$ is W or L-Nal2,
X$_2$ is G, V, A or S,
X$_3$ is S, D or A,
X$_4$ is C* or Abu,
X$_5$ is R—S, R—S-Nm, R—S—C*-G, R-Abu-Nm, R-Abu-C*-G, K-iPr-S-Nm or K-iPr-S—C*-G,
Abu corresponds to a 2-aminobutyric acid residue,
iPr corresponds to an isopropyl-lysine residue,
Nal2 corresponds to a 2-naphthylalanine,
Nm indicates that the COOH end has been replaced by a NH$_2$ end,
* indicates that when both X$_4$ and X$_5$ represent or comprise a cysteine residue said cysteine residues can be linked by a disulfide bond,
for promoting survival and/or growth and/or differentiation of progenitor cells or stem cells.

The peptide compound of the invention can be obtained in different ways: by chemical synthesis, by other methods based on recombinant technology and genetic constructs comprising a sequence or a fragment DNA that encode the peptide compounds. The oligopeptide according to the invention can be in deglycosylated or glycosylated form if necessary. In some cases, and depending on the preparation method, it may be necessary to renature certain tertiary structures of the oligopeptide.

In the invention, the "stem cells" are defined on the basis of two functional properties:
a seemingly unlimited capacity for self-renewal, and
the ability to generate multiple mature neural cell types.

Stem cells can be totipotent (the ability to produce all of the differentiated cells in an organism), pluripotent (the ability to produce all of the cells of the three germ layers: endoderm, mesoderm and ectoderm) or multipotent (the ability to differentiate into multiple, but limited cell types).

In the invention, the "progenitor cells" are early descendants of stem cells. Progenitors cells are proliferative cells with a limited capacity for self-renewal and they are often unipotent.

In an embodiment, the invention relates to the use of at least one peptide compound as defined above, said peptide compound comprising or consisting in:

$$X_1-S-X_2-W-S-X_3-X_4-S-X_5, \quad \text{(SEQ ID NO: 2)}$$

wherein:
X$_1$ is W or L-Nal2,
X$_2$ is G,
X$_3$ is S,
X$_4$ is C* or Abu,
X$_5$ is R—S, R—S-Nm, R—S—C*-G, R-Abu-Nm, R-Abu-C*-G, K-iPr-S-Nm or K-iPr-S—C*-G,
Abu corresponds to a 2-aminobutyric acid residue,
iPr corresponds to an isopropyl-lysine residue,
Nal2 corresponds to a 2-naphthylalanine,
Nm indicates that the COOH end has been replaced by a NH$_2$ end,
* indicates that when both X$_4$ and X$_5$ represent or comprise a cysteine residue said cysteine residues can be linked by a disulfide bond.

In an embodiment, the invention relates to the use of at least one peptide compound as defined above, said peptide compound comprising or consisting in:
W—S-G-W—S—S—[C/Abu]-S—R—S (SEQ ID NO: 3).

In an embodiment, the invention relates to the use of a peptide compound as defined above, said peptide compound having at least 90% identity with SEQ ID NO: 3.

Techniques for determining amino acid "sequence identity" are well known in the art. Typically, such techniques include determining the amino acid sequence encoded by a gene, and comparing this sequence to a second amino acid sequence. In general, "identity" refers to an exact amino acid-to-amino acid correspondence of two polypeptide sequences, respectively. Two or more sequences can be compared by determining their "percent identity." The percent identity of two amino acid sequences is the number of exact matches between two aligned sequences divided by the length of the shorter sequences and multiplied by 100. Numerous softwares are suitable for calculating the percent identity between sequences. For example, the BLAST software can be used with default parameters (genetic code=standard; filter=none; strand=both; cutoff=60; expect=10; Matrix BLOSUM62; Descriptions=50 sequences; sort by=HIGH SCORE; Databases=non-redundant, GenBank+EMBL+DDBJ+PDB+GenBank CDS translations+Swiss protein+Spupdate+PIR).

In an embodiment, the invention relates to the use of at least one peptide compound according as defined above, said peptide compound being selected from the group comprising:

$$W-S-G-W-S-S-C-S-R-S, \quad \text{(SEQ ID NO: 4)}$$

$$W-S-G-W-S-S-C-S-R-S-Nm, \quad \text{(SEQ ID NO: 5)}$$

-continued

```
                                            (SEQ ID NO: 6)
W-S-G-W-S-S-C-S-R-S-C-G, (SEQ ID NO: 7)
W-S-G-W-S-S-C^S-S-R-S-C^S-G, (SEQ ID NO: 8)
W-S-G-W-S-S-C-S-R-Abu-Nm, (SEQ ID NO: 9)
W-S-G-W-S-S-C-S-R-Abu-C-G, (SEQ ID NO: 10)
W-S-G-W-S-S-C^S-S-R-Abu-C^S-G, (SEQ ID NO: 11)
W-S-G-W-S-S-C-S-K-iPr-S-Nm, (SEQ ID NO: 12)
W-S-G-W-S-S-C-S-K-iPr-S-C-G, (SEQ ID NO: 13)
W-S-G-W-S-S-C^S-S-K-iPr-S-C^S-G, (SEQ ID NO: 14)
W-S-G-W-S-S-Abu-S-R-S, (SEQ ID NO: 15)
W-S-G-W-S-S-Abu-S-R-S-Nm, (SEQ ID NO: 16)
W-S-G-W-S-S-Abu-S-R-S-C-G, (SEQ ID NO: 17)
W-S-G-W-S-S-Abu-S-R-Abu-Nm, (SEQ ID NO: 18)
W-S-G-W-S-S-Abu-S-R-Abu-C-G, (SEQ ID NO: 19)
W-S-G-W-S-S-Abu-S-K-iPr-S-Nm, (SEQ ID NO: 20)
W-S-G-W-S-S-Abu-S-K-iPr-S-C-G, (SEQ ID NO: 21)
L-Nal2-S-G-W-S-S-C-S-R-S, (SEQ ID NO: 22)
L-Nal2-S-G-W-S-S-C-S-R-S-Nm, (SEQ ID NO: 23)
L-Nal2-S-G-W-S-S-C-S-R-S-C-G, (SEQ ID NO: 24)
L-Nal2-S-G-W-S-S-C^S-S-R-S-C^S-G, (SEQ ID NO: 25)
L-Nal2-S-G-W-S-S-C-S-R-Abu-Nm, (SEQ ID NO: 26)
L-Nal2-S-G-W-S-S-C-S-R-Abu-C-G, (SEQ ID NO: 27)
L-Nal2-S-G-W-S-S-C^S-S-R-Abu-C^S-G, (SEQ ID NO: 28)
L-Nal2-S-G-W-S-S-C-S-K-iPr-S-Nm, (SEQ ID NO: 29)
L-Nal2-S-G-W-S-S-C-S-K-iPr-S-C-G, (SEQ ID NO: 30)
L-Nal2-S-G-W-S-S-C^S-S-K-iPr-S-C^S-G, (SEQ ID NO: 31)
L-Nal2-S-G-W-S-S-Abu-S-R-S, (SEQ ID NO: 32)
L-Nal2-S-G-W-S-S-Abu-S-R-S-Nm, (SEQ ID NO: 33)
L-Nal2-S-G-W-S-S-Abu-S-R-S-C-G, (SEQ ID NO: 34)
L-Nal2-S-G-W-S-S-Abu-S-R-Abu-Nm, (SEQ ID NO: 35)
L-Nal2-S-G-W-S-S-Abu-S-R-Abu-C-G, (SEQ ID NO: 36)
L-Nal2-S-G-W-S-S-Abu-S-K-iPr-S-Nm, (SEQ ID NO: 37)
L-Nal2-S-G-W-S-S-Abu-S-K-iPr-S-C-G,
``` wherein $^s$ indicates that cysteine residues are linked by a disulfide bond, preferably selected from the group comprising:

```
                                            (SEQ ID NO: 6)
W-S-G-W-S-S-C-S-R-S-C-G, (SEQ ID NO: 7)
W-S-G-W-S-S-C^S-S-R-S-C^S-G, (SEQ ID NO: 15)
W-S-G-W-S-S-Abu-S-R-S-Nm,
``` wherein $^s$ indicates that cysteine residues are linked by a disulfide bond.

SEQ ID NO: 6 corresponds to the sequence of the peptide referred to as NX210.

SEQ ID NO:7 corresponds to the sequence of the peptide referred to as NX218.

SEQ ID NO: 15 corresponds to the sequence of the peptide referred to as NS640.

In an embodiment, the invention relates to the use of at least one peptide compound as defined above, wherein said progenitor cells and said stem cells are mammal cells, preferably human cells.

In an embodiment, the invention relates to the use of at least one peptide compound as defined above, wherein said stem cells are mesenchymal stem cells or embryonic stem cells, preferably mesenchymal stem cells.

In the invention, the expression "embryonic stem cells" refers to stem cells that are derived from the inner cell mass of a blastocyst.

Embryonic stem cells (ESC) are totipotent, meaning they can differentiate to form all cell types of an organism.

In a preferred embodiment, the invention relates to the use of at least one peptide compound as defined above, wherein said stem cells are human embryonic stem cells (hESC) lines.

In a preferred embodiment, the invention relates to the use of at least one peptide compound as defined above, wherein said stem cells are human embryonic stem cells (hESC) lines that have not been initially obtained by methods involving the destruction of human embryos.

In the invention, the expression "mesenchymal stem cells" (MSC) refers to adult stem cells that are present in multiple tissues.

Mesenchymal stem cells (MSCs) are an example of tissue or "adult" stem cells. They are multipotent, meaning they can produce more than one type of specialized cell of the body, but not all types. They are able to differentiate into mesodermal lineages (osteogenic, adipogenic, chondrogenic), but also towards non-mesodermal derivatives (e.g. neural cells).

In an embodiment, the invention relates to the use of at least one peptide compound as defined above, wherein said mesenchymal stem cells have been obtained from bone marrow, umbilical cord blood, fat tissue, dental pulp or muscle.

In an embodiment, the invention relates to the use of at least one peptide compound as defined above, wherein said peptide compound is used to promote differentiation of progenitor cells or stem cells, preferably mesenchymal stem cells, into neural cells.

In the invention, the expression "neural cells" refers to cells that derive from neural stem cells. Neural cells correspond primarily to neurons, astrocytes and oligodendrocytes.

The differentiation into neural cells can be evaluated through the expression of neural markers by stem cells or by progenitor cells.

For example, neural markers include, but are not limited to
- GFAP (Glial Fibrillary Astrocyte Protein): a protein that is expressed by glial cells and astrocytes,
- Musashi 1: a protein that binds RNA and that is found in progenitor cells,
- Nestin: a protein that can be found in intermediate filaments in neural progenitors,
- βIII-tubulin: a protein found in microtubules of neural cells at an intermediate stage of differentiation,
- MAP-2 (Microtubule Associated Protein): a protein found in microtubules in neurites or dendrites of mature neural cells.

The differentiation into neural cells can also be evaluated through the neuritic sprouting, that means the extensions of a neuron (axonal or dendritic extensions).

In an embodiment, the invention relates to the use of at least one peptide compound as defined above, wherein said peptide compound is used to promote survival of progenitor cells or stem cells, preferably mesenchymal stem cells or neural stem cells.

In an embodiment, the invention relates to the use of at least one peptide compound as defined above, wherein said peptide compound is used to promote growth of progenitor cells or stem cells, preferably mesenchymal stem cells.

In an embodiment, the invention relates to the use of at least one peptide compound as defined above, said peptide compound being selected from the group comprising:

$$W\text{-}S\text{-}G\text{-}W\text{-}S\text{-}S\text{-}C\text{-}S\text{-}R\text{-}S\text{-}C\text{-}G, \quad (\text{SEQ ID NO: 6})$$

$$W\text{-}S\text{-}G\text{-}W\text{-}S\text{-}S\text{-}C^S\text{-}S\text{-}R\text{-}S\text{-}C^S\text{-}G, \quad (\text{SEQ ID NO: 7})$$

$$W\text{-}S\text{-}G\text{-}W\text{-}S\text{-}S\text{-}Abu\text{-}S\text{-}R\text{-}S\text{-}Nm, \quad (\text{SEQ ID NO: 15})$$

wherein $^S$ indicates that cysteine residues are linked by a disulfide bond, for promoting differentiation of mesenchymal stem cells into neural cells.

In an embodiment, the invention relates to the use of at least one peptide compound as defined above, wherein said progenitor cells or said stem cells are grown in a culture system containing said peptide compound.

In the invention, the expression "culture system" can refer to a variety of culture materials, such as a medium, a substrate, a support or a flask. In particular, a culture system can also refer to a combination of culture materials, such as a flask containing a medium.

In an embodiment, the invention relates to the use of at least one peptide compound as defined above, wherein said progenitor cells or said stem cells are grown in a culture system in presence of 0.02 µg/ml to 20 µg/ml or 1 to 1000 µg/cm$^2$, preferably from 0.2 µg/ml to 2 µg/ml or 10 to 500 µg/cm$^2$, of the peptide compound.

In an embodiment, the invention relates to the use of at least one peptide compound as defined above, wherein said progenitor cells or said stem cells are grown in a culture system in presence of 0.02, 0.05, 0.1, 0.2, 0.5, 1, 2, 5, 10, 15 or 20 µg/ml.

In an embodiment, the invention relates to the use of at least one peptide compound as defined above, wherein said progenitor cells or said stem cells are grown in a culture system in presence of 1, 2, 5, 10, 20, 30, 40, 50, 60, 70, 80, 90, 100, 200, 300, 400, 500, 600, 700, 800, 900 or 1000 µg/cm$^2$ of the peptide compound.

In an embodiment, the invention relates to the use of at least one peptide compound as defined above, wherein said progenitor cells or said stem cells are grown in a culture medium containing the peptide compound, said culture medium further containing at least one growth factor, preferably selected from the group comprising bFGF, LIF, Activin-A, TGF, Wnt, Oct-4, Sox-2, BMP-4, Nanog, Shh, PDGF, retinoic acid, EGF, IGF1, IGF2, HGF, VEGF, insulin and transferrin.

In an embodiment, said progenitor cells or stem cells are grown in a culture medium containing the peptide compound and containing from 0.01 ng/ml to 1000 ng/ml, preferably from 1 ng/ml to 100 ng/ml, more preferably from 1 ng/ml to 10 ng/ml, of at least one growth factor.

In an embodiment, said progenitor cells or stem cells are grown in a culture medium containing the peptide compound and containing 0.01, 0.02, 0.05, 0.1, 0.2, 0.5, 1, 2, 5, 10, 20, 50, 100, 200, 500 or 1000 ng/ml of at least one growth factor.

In an embodiment, the invention relates to the use of at least one peptide compound as defined above, wherein said progenitor cells or said stem cells are grown in a culture medium containing the peptide compound, said culture medium further containing 0 to 20% of Fetal Bovine Serum (v/v), preferably from 2% to 10%.

In an embodiment, the invention relates to the use of at least one peptide compound as defined above, wherein said progenitor cells or said stem cells are grown in a culture medium containing the peptide compound, said culture medium further containing 0, 1, 2, 3, 4, 5, 6, 7, 8, 9, 10, 11, 12, 13, 14, 15, 16, 17, 18, 19 or 20% of Fetal Bovine Serum (v/v).

In an embodiment, the invention relates to the use of at least one peptide compound as defined above, wherein mesenchymal stem cells are grown in a culture medium containing the peptide compound, said culture medium further containing bFGF and Fetal Bovine Serum,
  preferably in a culture medium containing:
  1 to 100 ng/ml of bFGF, and
  1 to 10% of Fetal Bovine Serum (v/v).

In an embodiment, the invention relates to the use of at least one peptide compound as defined above, wherein said peptide compound corresponds to SEQ ID NO: 6, SEQ ID NO: 7 or SEQ ID NO: 15 and mesenchymal stem cells are grown in a culture medium containing the peptide compound, said culture medium further containing bFGF and Fetal Bovine Serum,
  preferably in a culture medium containing:
  1 to 100 ng/ml of bFGF, and
  1 to 10% of Fetal Bovine Serum (v/v).

In an embodiment, the invention relates to the use of at least one peptide compound as defined above, wherein said peptide compound corresponds to SEQ ID NO: 6 and mesenchymal stem cells are grown in a culture medium containing the peptide compound, said culture medium further containing bFGF and Fetal Bovine Serum, preferably in a culture medium containing:
  1 to 100 ng/ml of bFGF, and
  1 to 10% of Fetal Bovine Serum (v/v).

In an embodiment, the invention relates to the use of at least one peptide compound as defined above, wherein said peptide compound corresponds to SEQ ID NO: 7 and mesenchymal stem cells are grown in a culture medium containing the peptide compound, said culture medium further containing bFGF and Fetal Bovine Serum, preferably in a culture medium containing:
  1 to 100 ng/ml of bFGF, and
  1 to 10% of Fetal Bovine Serum (v/v).

In an embodiment, the invention relates to the use of at least one peptide compound as defined above, wherein said peptide compound corresponds to SEQ ID NO: 15 and mesenchymal stem cells are grown in a culture medium containing the peptide compound, said culture medium further containing bFGF and Fetal Bovine Serum, preferably in a culture medium containing:
  1 to 100 ng/ml of bFGF, and
  1 to 10% of Fetal Bovine Serum (v/v).

In an embodiment, the invention relates to the use of at least one peptide compound as defined above, wherein said progenitor cells or said stem cells are grown on a support containing the peptide compound, said peptide compound being preferably coated on the support.

In another aspect, the invention also relates to a method for promoting survival and/or growth and/or differentiation of progenitor cells or stem cells comprising a step of culture of said progenitor cells or said stem cells in presence of at least one peptide compound as defined above.

In another aspect, the invention also relates to a kit comprising:
  at least one peptide compound as defined above
  a culture system suitable for growth of progenitor cells and/or stem cells,
  and possibly, progenitor cells and/or stem cells.

The kit of the invention can be used to test the therapeutic efficacy of products on stem cells.

In an embodiment, the invention relates to a kit as defined above containing more than one peptide compound.

For example, the kit of the invention can contain a mix of 2, 3, 4, 5, 6, 7, 8, 9, 10 or more different peptide compounds.

In an embodiment, the invention relates to a kit as defined above that further comprises a multi-well plate treated, or not treated, to enable cell adhesion.

In an embodiment, the invention relates to a kit as defined above wherein said culture medium comprises gelatin and/or growth factors such as bFGF, LIF, Activin-A, TGF, Wnt, Oct-4, Sox-2, BMP-4, Nanog, Shh, PDGF, retinoic acid, EGF, IGF1, IGF2, HGF, VEGF, insulin and transferrin.

The invention is illustrated by the following figures and examples. These examples are not intended to be limitations of the invention.

EXAMPLES

Example 1: Early Differentiation

Materials and Methods 129S v/J embryonic stem cells (ESCs) were seeded at a concentration of $0.7 \times 10^6$ cells in 35 mm diameter Petri dishes covered with a gelatin substrate.

The culture medium used was the Glasgow's minimal essential medium (G-MEM) supplemented with N2 supplement.

To enable differentiation of ESCs into neuroepithelial progenitors, the culture medium was deprived of LIF (Leukemia Inhibitory factor) because LIF is a key factor of the self-renewal of ESCs.

The various tests were carried out in absence of serum because serum limits the possibility to specifically orientate the differentiation and it could hide, or at least reduce, the effects of the peptide compound of the invention.

ESCs were grown in the culture medium as defined above with addition of 0.5 mg/ml NX210 (SEQ ID NO: 6) at day 1, 3 and 5.

Then, cultures were fixed with 4% paraformaldehyde after 7 days of culture.

To analyze the differentiation of ESCs into neuroepithelial progenitors and into differentiated neurons, the various cell types were visualized by immunocytochemistry:
  using a primary anti-nestin antibody (nestin=intermediate filament protein), specific of neuroepithelial progenitors, and
  using a primary anti-MAP2 antibody (MAP2=microtubule associated protein 2), specific of dendrites, and thus specific of differentiated neurons.

The total number of cells was measured by labelling nuclei using bisbenzimide/Hoechst 33342, a fluorescent dye with an affinity for DNA that is commonly used to color nuclei in blue.

Results

Figure 1:
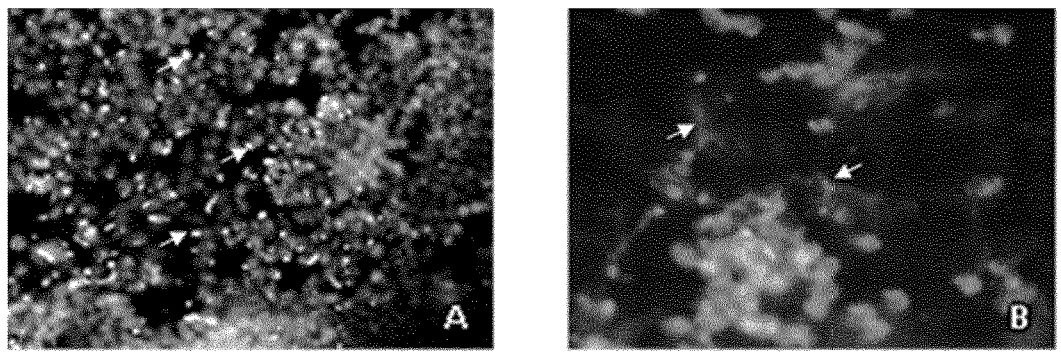
FIG. 1. Expression of the nestin protein in ESCs cultivated on gelatine during 7 days and treated with 0.5 mg/ml NX210 peptide. (A) Control untreated culture shows a greater number of Nestin+ cells (brightest spots, white arrows) compared to the NX210-treated culture (B) with few Nestin+cells (white arrows).

After 7 days of culture, it has been observed that the population of ESCs expressing the nestin protein is reduced in the culture in the presence of NX210 (SEQ ID NO: 6)

compared to the population of ESCs cells expressing the nestin protein in the culture in the absence of NX210 (SEQ ID NO: 6) (FIG. 1).

Figure 2:
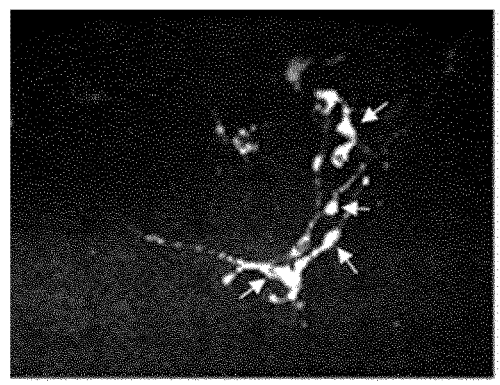
FIG. 2. Expression of MAP2 in ESCs after 5 days in the presence of 0.5 mg/ml NX210 peptide. MAP2$^+$ cells (white arrows) are only observed in presence of NX210 compared to control culture where no MAP2 expressing cells have been observed.

Indeed, in the absence of NX210 (SEQ ID NO: 6), it is observed some cells expressing the nestin protein (characteristic of neuroepithelial progenitors) but no cells expressing the MAP2 protein (that means no differentiated neurons), whereas in the presence of NX210, it is observed some cells expressing the MAP2 protein (FIG. 2).

Thus, the differentiation has reached rapidly a more advanced stage in the presence of NX210 (SEQ ID NO: 6).

These results demonstrate that NX210 (SEQ ID NO: 6) induces a preferential orientation of ESCs to the neuronal differentiation pathway in terms of kinetics.

Example 2: Selection of Neuroepithelial Progenitors

Materials and Methods

For these experiments, the differentiation of ESCs was preferably orientated to the neuronal differentiation pathway, according to the protocol adapted from Okabe et al., (Mechanisms of Development, 59:89-102, 1996).

In brief, to start the differentiation, the ESCs were grown on gelatin without LIF for two days. The cells were carefully trypsinated to collect small ESC aggregates. Then, these aggregates were transferred on a Petri dish without any coating to produce non-adherent spherical cell bodies, namely the embryoid bodies (EB).

After 5 days of culture, the EB were transferred onto a new Petri dish covered with gelatin to enable cell adhesion.

After 24 h of culture, the culture medium with fetal bovine serum 10% was replaced by a culture medium serum free to select neuroepithelial progenitors and the peptide NX210 (SEQ ID NO: 6) was added in the culture medium at a concentration of 0.5 mg/ml.

After 6 days of culture, the maximal content of cells expressing the nestin protein (a cytoskeletal protein specific of the neuroepithelial progenitors) was reached.

The cell population enriched for neuroepithelial progenitors was then trypsinated and seeded at a concentration of $1 \times 10^5$ cells/cm$^2$ on a substrate made up of a polyornithine and laminin mix.

After 2 days of culture in the presence of FGF2 (Fibroblast Growth Factor 2) to develop the pool of precursors, the cells were fixed and treated prior to Nestin immunostaining.

Results

Figure 3:
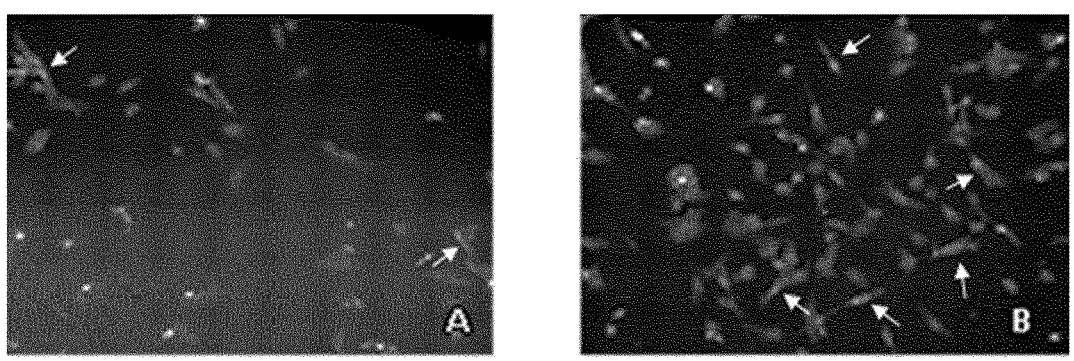
FIG. 3. Expression of the Nestin protein showing more neuronal precursors cells (white arrows) in treated-culture (B) compared to untreated conditions (A).

More cells expressing the Nestin protein have been observed in the culture treated with NX210 (SEQ ID NO: 6) in comparison to the untreated culture (FIG. 3).

The production of a differentiation marker such as Nestin in the presence of NX210 (SEQ ID NO: 210) suggests an accelerated differentiation of ESCs into the neuronal pathway.

Thus, during the selection of the neuroepithelial progenitors, NX210 promotes a more efficient response to the specific stimulation by FGF2.

Example 3: Neural Differentiation of Human Mesenchymal Stem Cells

Materials and Methods

Adult human bone marrow mononuclear cells Ficoll-extracted from two donors were obtained from Lonza. Cells were passaged once a week. The human mesenchymal stem cells (hMSC) were selected by plastic adherence and expanded by plating 50 000 cells/cm$^2$ in Modified Eagle Medium Alpha (MEMalpha, MacoPharma) supplemented with 10% Fetal Bovine Serum (FBS, PAA Laboratoires) and 0.1% Penicilline/Streptomycine (P/S, Lonza). The culture medium was changed after 3 days and then every day. After 2 to 5 weeks of culture at 37° C. in a humid environment and under 5% $CO_2$, hMSC were harvested by trypsinization. The phenotype was confirmed by FACS analysis (BD Bioscience, BD LSR II) with CD73, CD90 and CD105 (positive), as well as CD34 and CD45 (negative) (Table 1).

TABLE 1

Immunophenotyping of hMSCs obtained from the two donors. Differences observed in the two patients are standard inter-individual variability.

| Cell surface marker | Patient n° 1 | Patient n° 2 |
|---|---|---|
| CD105 | 42.5% | 40.4% |
| CD73 | 57.9% | 86.8% |
| CD90 | 58.3% | 87.0% |
| CD34 | 2.8% | 11.5% |
| CD45 | 12.8% | 41.6% |

Moreover, the self-renewal capacity of cells was confirmed by the colony forming units-fibroblast assay (CFU-F). For this assay, hMSCs were seeded at two different densities: 20,000 cells/cm$^2$ and 60,000 cells/cm$^2$ in 25 cm$^2$ flasks with the complete medium described above. Seven and 10 days later, the number of CFU-F colonies with more than 50 cells (large colonies), less than 25 cells (small colonies) and between 25 and 50 cells (medium size colonies) were counted.

TABLE 2

Results of the CFU-F assay.

| Number of plated cells | Average count of CFU-F at J7 | | | | | | Average count of CFU-F at J10 | | | | | | Total at D 10 | |
|---|---|---|---|---|---|---|---|---|---|---|---|---|---|---|
| | <25 | | 25-50 | | >50 | | <25 | | 25-50 | | >50 | | | |
| | P1 | P2 | P1 | P2 | P1 | P2 | P1 | P2 | P1 | P2 | P1 | P2 | P1 | P2 |
| $0.5 \cdot 10^6$ | 13 | 55 | 5.5 | 10.5 | 2.5 | 2 | 10 | 17.5 | 6.5 | 14.5 | 15 | 40.5 | 31.5 | 72.5 |
| $1.5 \cdot 10^6$ | 42.5 | 106.3 | 11 | 79 | 1 | 6 | 21.5 | 28 | 16.5 | 30 | 30 | 65 | 68 | 123 |

From D7 to D10, sample from patient n° 2 forms a higher number of CFU-F than from patient 1 for each type of colony (small, medium, and large). At D10, the total number of CFU-Fs is greater for patient n° 2 suggesting better proliferative capacities. Average count of CFU-F = measurements averaged over 2 to 3 counting.
P1 = Patient n° 1.
P2 = Patient n° 2.

To investigate the neural differentiation capacity of the peptides, 25 cm² flasks and 12-wells culture plates were coated with sterile aqueous solutions of either NX210 or NS640 at a concentration of 80 µg/cm². Coatings were carried out at 37° C. and 5% $CO_2$ over-night prior to cell plating.

On Day 0 (D0), hMSC were seeded at a concentration of 3,000 cells/cm² in pre-coated 25 cm² flasks or 12-well culture plates in complete medium and culture was placed at 37° C. in a humid environment and under 5% $CO_2$. After 24 h, medium was changed and replaced by different combinations of media containing either: MEMalpha-bFGF 12.5 ng/mL-FBS 2%-P/S 0.1%; MEMalpha-bFGF 12.5 ng/mL-FBS 10%-P/S 0.1%; MEMalpha-FBS 2%-P/S 0.1% (control condition); MEMalpha-FBS 10%-P/S 0.1% (control condition). The cells were placed at 37° C. in a humid environment and under 5% $CO_2$, and medium was changed twice a week. On Day 8, medium was replaced by medium containing ATRA in the place of bFGF and thus was changed with: MEMalpha-ATRA 201 µM-FBS 2%-P/S 0.1%; MEMalpha-ATRA 20 µM-FBS 10%-P/S 0.1%; MEMalpha-FBS 2%-P/S 0.1% (control condition); MEMalpha-FBS 10%-P/S 0.1% (control condition). The cells were placed at 37° C. in a humid environment and under 5% $CO_2$. Medium was changed twice a week. On Day 15 (D15), cells were harvested by trypsinization for mRNA extraction or fixed immunocytochemical analysis.

Assessment of differentiation was performed by gene expression after extraction of mRNA at various time point (DO, D1, D8 and D15), and immunocytochemical analysis performed at the end of the culture period (D15).

Immunocytochemical analyses were carried out on cells fixed in 4% paraformaldehyde and using standard protocols. After blocking with Triton 1×0.1%/BSA 5% during 30 min, cells were incubated with antibodies directed against Nestin (Millipore) or MAP-2 (Sigma) overnight at +4° C. After washing, appropriate FITC or Cyandidine-5 labelled secondary antibody are added. Nuclei were counterstained with Hoescht 33258 (Sigma). Obervations were performed using Leica TCS LSI system.

Total RNA was extracted using RNAeasy total purification kit following instructions of the manufacturer (Qiagen). cDNA were generated using a High-Capacity cDNA Reverse Transcription kit (Applied Biosystems) as described by the manufacturer.

The expression levels of genes (GFAP, Musashi 1, Nestin, Beta3-Tubuline, MAP-2 and GAPDH) were analyzed by real-time PCR using TaqMan gene Expression Master Mix (Applied Biosystems) on the Applied Biosystems 7900 Real time PCR system (Life technologies). Samples were analyzed in triplicates. Data were normalized using the GAPDH gene as an internal control and relative quantification (RQ) of the genes in a sample was determined according to the equation $2^{-\Delta ct}$.

Results

Figure 4:
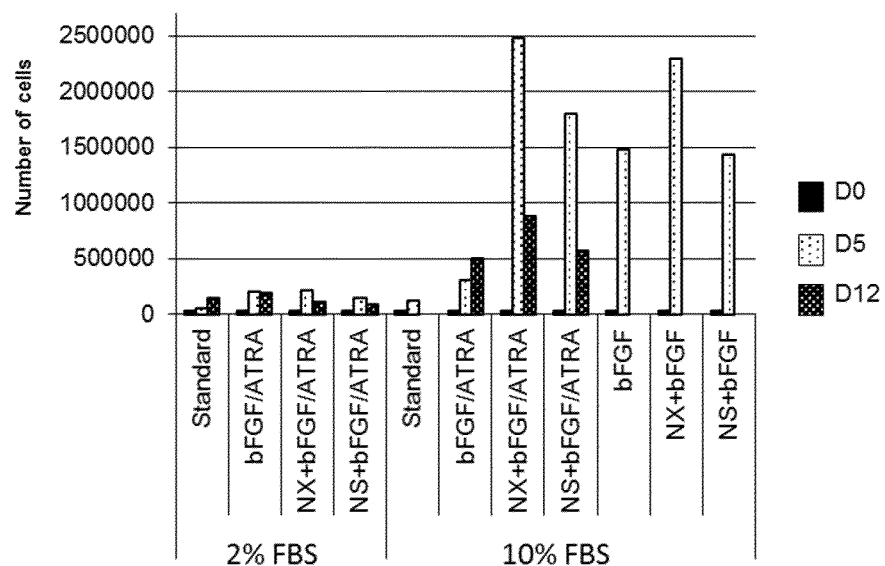
FIG. 4. Cell proliferation depending of the culture conditions.
Figure 4:
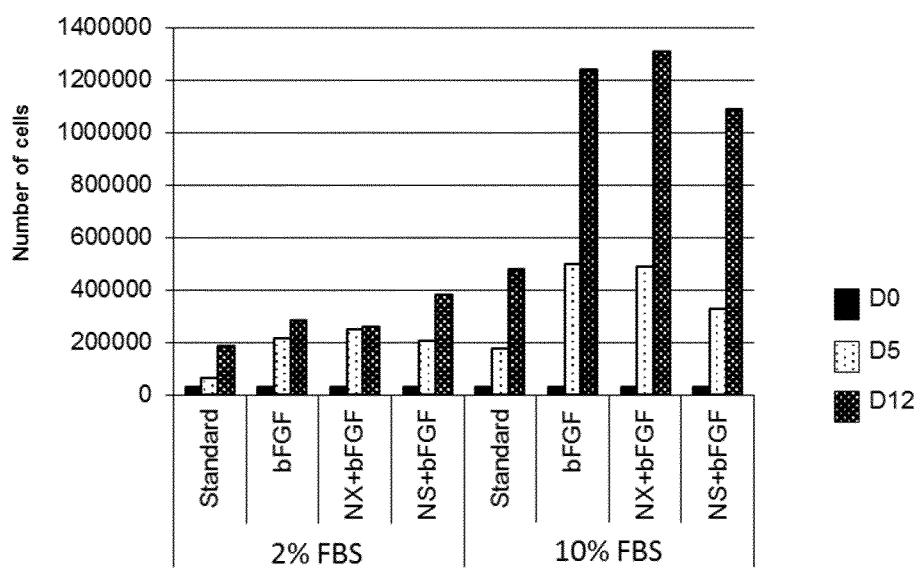

Despite inter-patient variations, number of MSCs is increased in presence of 10% FBS compared to 2% FBS. bFGF has a positive effect on cell proliferation whatever the FBS concentration. Moreover, add-on of ATRA (from J5) leads to small difference in the presence of 2% FBS and a decrease of the number of MSC in presence of 10% FBS (FIG. 4). NX210 or NS640 have no effect on proliferation whatever the conditions tested.

The protocols tested do not seem to favor a differentiation of MSCs in the glial pathway. The expression of GFAP was therefore not quantified subsequently.

Figure 5:
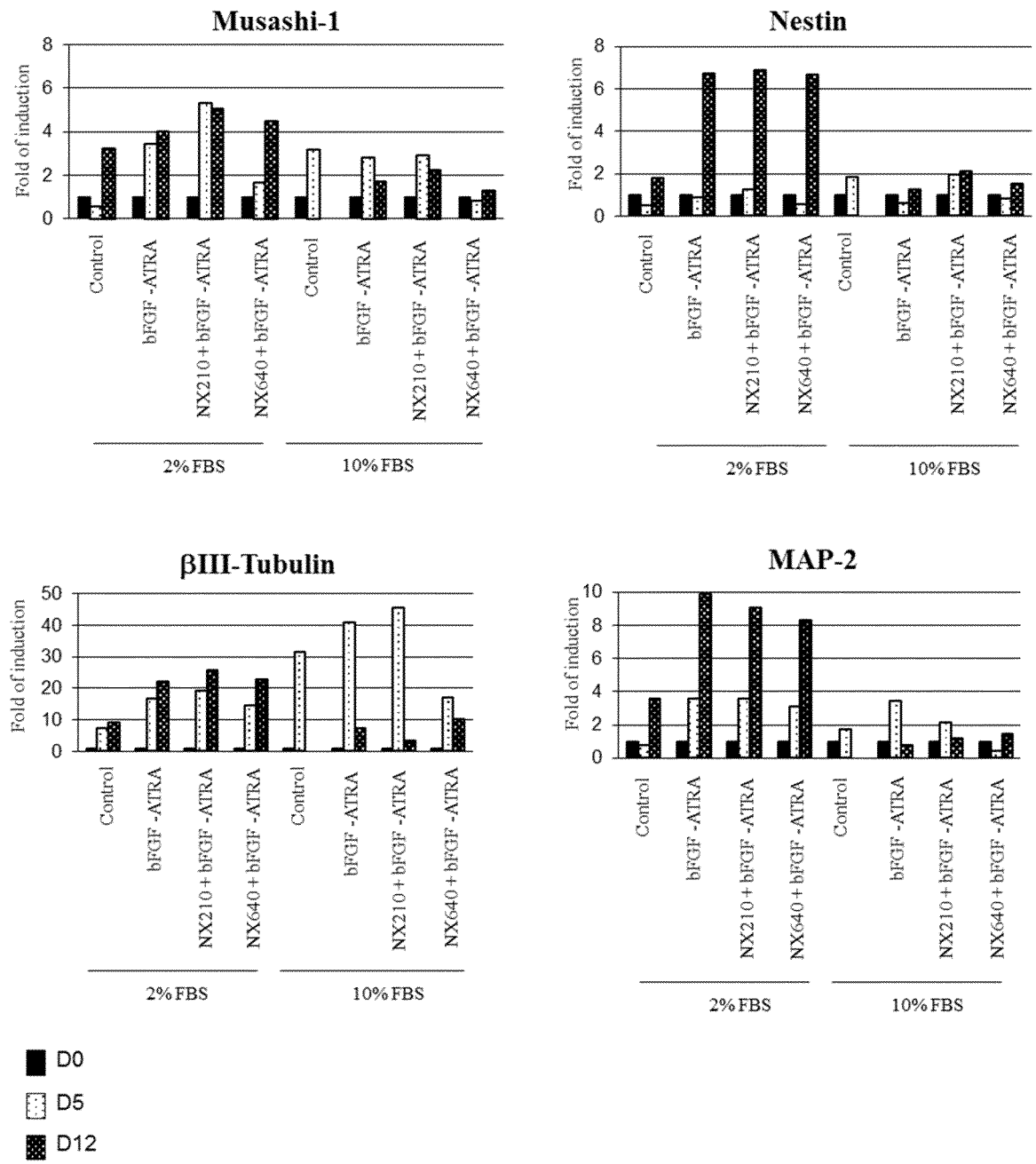
FIG. 5. Gene expression analysis performed on hMSCs from patient no. 1 grown in presence of bFGF and ATRA.

Sequential differentiation by bFGF and then ATRA (from J5) in the presence of 2% FBS leads to an increase in the gene expression of Nestin (×6.7 vs ×1.8), βIII-Tubulin (×22 vs ×9.2) and MAP-2 (×9.9 vs ×3.5) compared to control conditions. NX210 or NS640 does not modify this increase. In the presence of 10% FBS, the increase in expression is less marked. NX210 and NS640 have a moderate effect that is observed by increasing MAP-2 and Nestin expression (×1.21 and 1.46 vs ×0.75, ×2 and 1.5 vs ×1.2 respectively) (FIG. 5).

Figure 6:
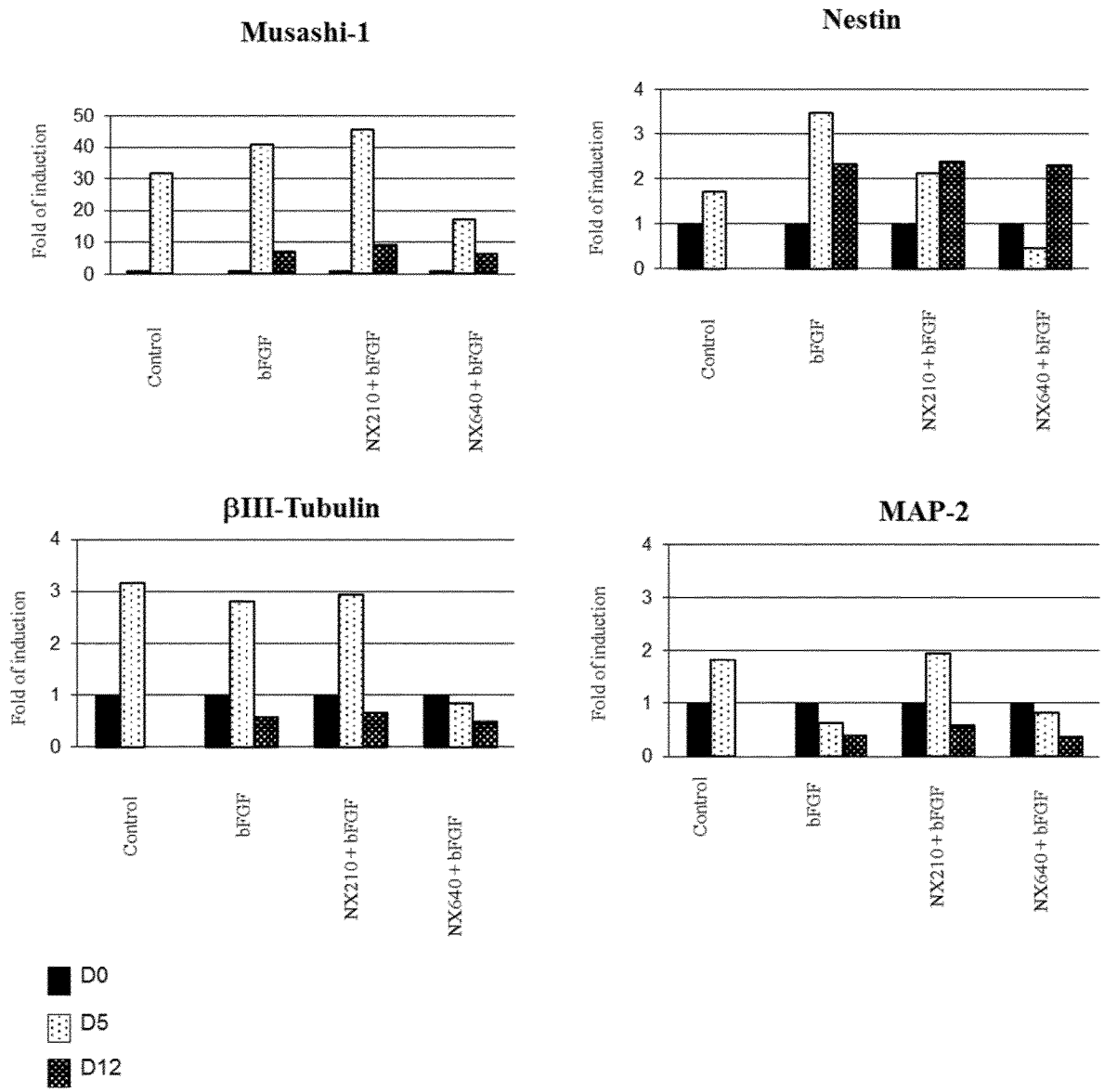
FIG. 6. Gene expression analysis performed on hMSCs from patient no. 1 grown in presence of bFGF 10% without ATRA.

For cells from patient no. 1, culture in presence of bFGF leads to a decrease in Musashi-1 and Nestin expression and to an increase in expression of βIII Tubulin and MAP-2 (respectively ×9.3 and ×2.3 with respect to the J0). At day 5, presence of NX210 and NX640 lead to an increase of Nestin expression compared to bFGF alone (×2 vs ×0.6 in the bFGF condition without NX210 or NX640 treatment) (FIG. 6).

Figure 7:
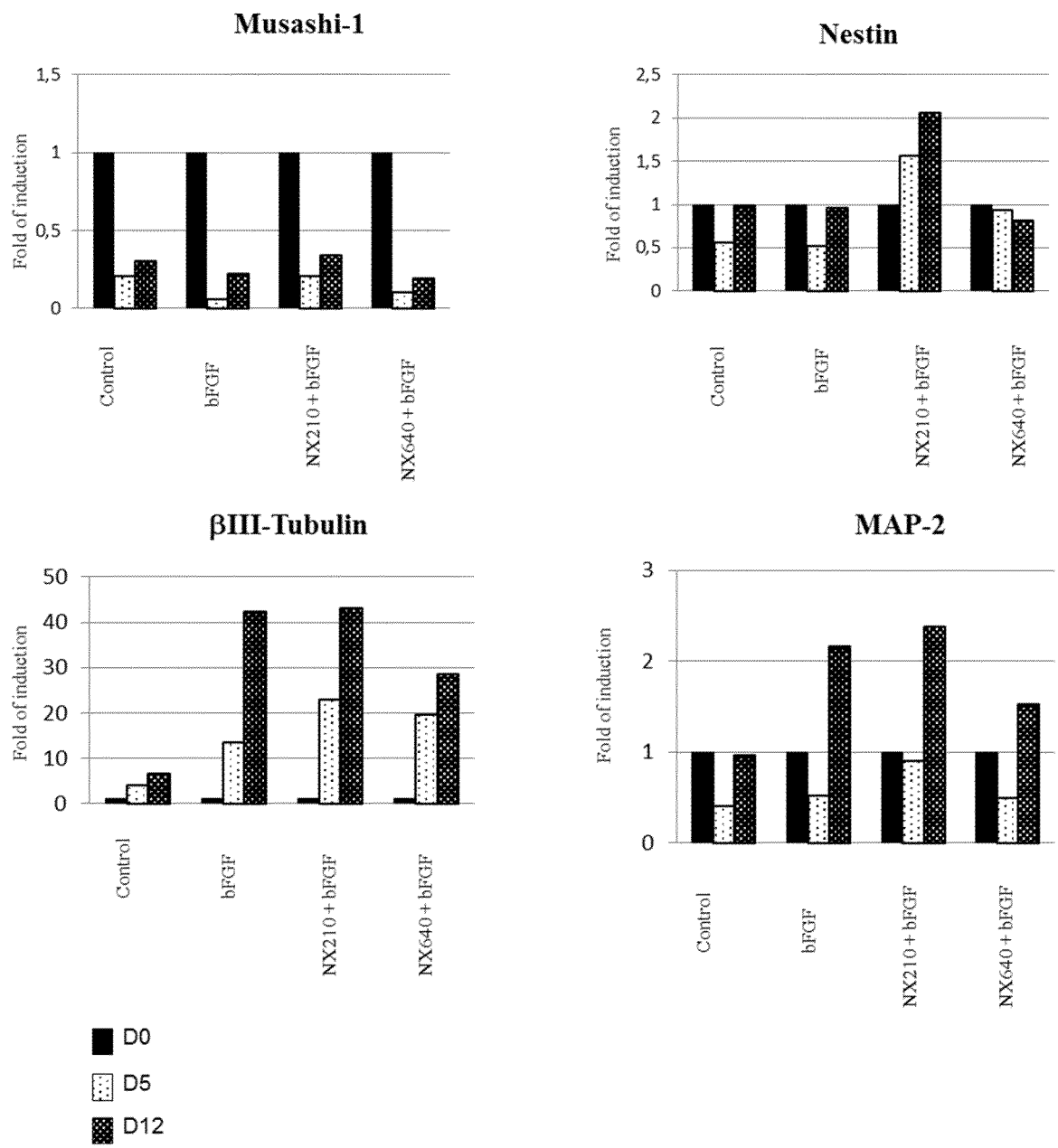
FIG. 7. Gene expression analysis performed on hMSCs from patient no. 2 grown in presence of bFGF 10% without ATRA.

Similarly to patient no. 1, culture of hMSCs from patient no. 2 in presence of bFGF leads to a decrease in Musashi-1 and Nestin expression and to an increase in expression of (3111 Tubulin and MAP-2 (respectively ×9.3 and ×2.3 with respect to the J0). Presence of NX210 leads to an increase of Nestin expression compared to bFGF alone (×1.95 vs ×0.6 in the bFGF condition without coating). Moreover, βIII-Tubuline is also maximized in presence of NX210 or NX640 after 5 days of culture. Whereas MAP-2 expression is decreased in with conditions bFGF alone, expression of this gene was increased at D5 in presence of NX210 (FIG. 7).

The results of the gene expression for Musashi-1, Nestin, βIII-Tubulin and MAP-2 are summarized in Table 3.

TABLE 3

Induction of gene expression.

| | | Musashi-1 | | Nestin | | βIII-Tubulin | | MAP-2 | |
| --- | --- | --- | --- | --- | --- | --- | --- | --- | --- |
| | | P1 | P2 | P1 | P2 | P1 | P2 | P1 | P2 |
| 2% FBS | bFGF | + | − | − | − | ++ | + | + | + |
| | NX210 + bFGF | ++ | − | − | + | ++ | + | + | − |
| | NS640 + bFGF | − | − | − | − | ++ | + | + | − |
| 10% FBS | bFGF | + | − | − | − | ++ | + | + | + |
| | NX210 + bFGF | + | − | + | + | ++ | + | + | + |
| | NS640 + bFGF | + | − | − | − | + | + | + | + |

P1 = Patient n° 1.
P2 = Patient n° 2.

Figure 8:
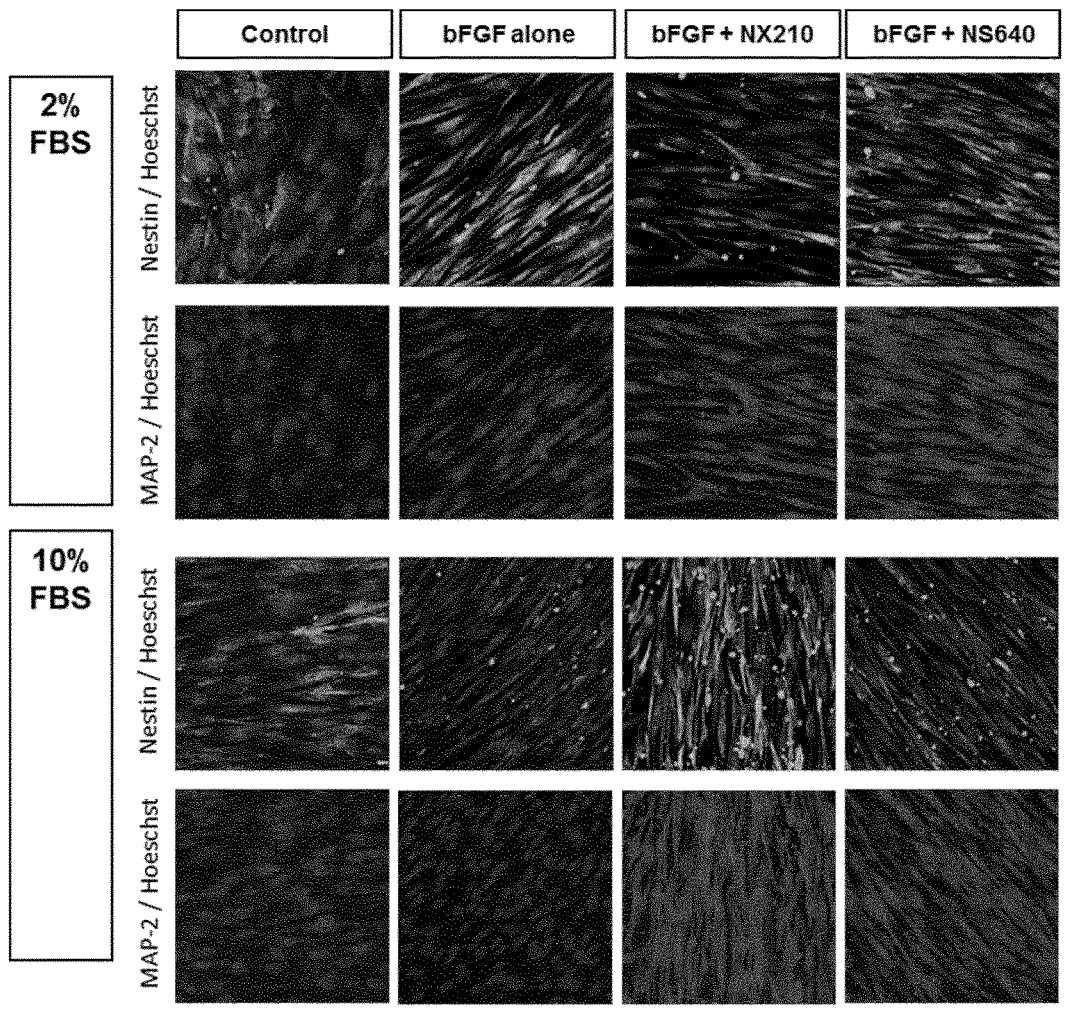
FIG. 8. Immunocytochemical analysis of hMSCs after 12 days of culture in the different conditions.

The addition of bFGF in the presence of 2% FBS increases the expression of Nestine and MAP-2 markers. In this condition, immunocytochemistry analysis showed a stronger staining when NX210 or NS640 are present. In 10% FBS condition, bFGF increases Nestine expression compared to the control condition, and this increase is maximized with NX210 or NX640 (increase of staining intensity). Only presence of NX210 and NX640 makes possible to observe MAP-2 protein presence (FIG. 8).

Figure 9:
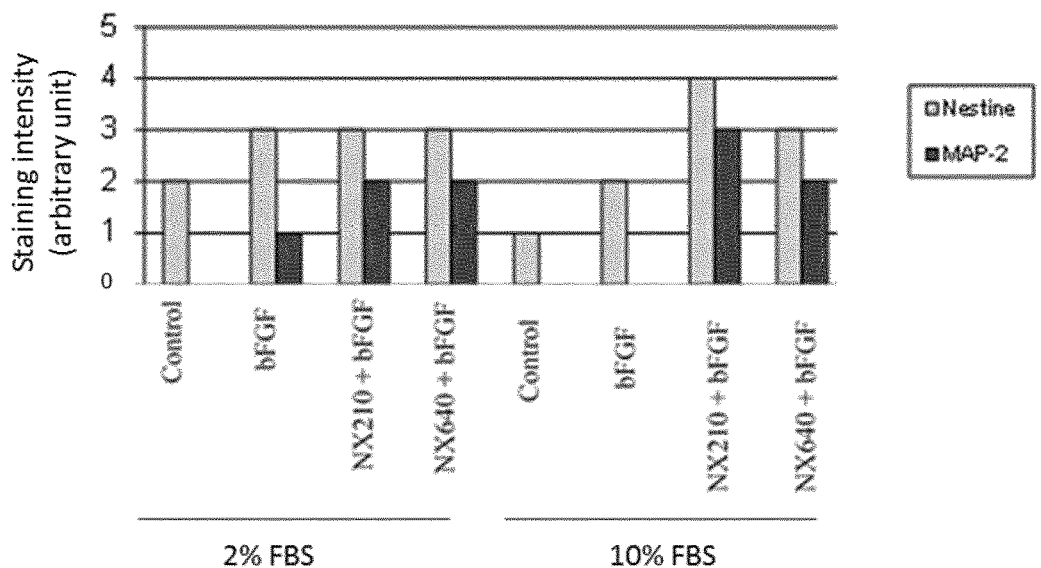
FIG. 9. Fluorescence intensity of MAP-2 and Nestin immunolabelling.

Gradations in the staining intensity corresponding to the expression of Nestin or MAP-2 were observed depending on the culture conditions (FIG. 9).

The invention claimed is:

1. An in vitro method for promoting differentiation of human mesenchymal stem cells (hMSCs) into neural cells, said method comprising:
   (a) culturing said human mesenchymal stem cells in a medium comprising fetal bovine serum (FBS) for at least two weeks;
   (b) coating a culture device with NX210 at a concentration of 80 μg/cm2; and
   (c) seeding the human mesenchymal stem cells of (a) on the coated device and culturing the seeded human mesenchymal stem cells in a medium comprising 12.5 ng/ml of bFGF and 10% FBS for at least 5 days;
   wherein said method leads to an increase in the gene expression of Nestin, βIII-Tubuline and MAP-2 in the human mesenchymal stem cells of (c).

2. The method according to claim 1, wherein said human mesenchymal stem cells have been obtained from bone marrow, umbilical cord blood, fat tissue, dental pulp, or muscle.

* * * * *

SEQUENCE LISTING

<160> NUMBER OF SEQ ID NOS: 37

<210> SEQ ID NO 1
<211> LENGTH: 9
<212> TYPE: PRT
<213> ORGANISM: Artificial Sequence
<220> FEATURE:
<223> OTHER INFORMATION: Peptide compound
<220> FEATURE:
<221> NAME/KEY: misc_feature
<222> LOCATION: (1)..(1)
<223> OTHER INFORMATION: X is W or L-Nal2
<220> FEATURE:
<221> NAME/KEY: misc_feature
<222> LOCATION: (3)..(3)
<223> OTHER INFORMATION: X is G, V, A, S or Abu
<220> FEATURE:
<221> NAME/KEY: misc_feature
<222> LOCATION: (6)..(6)
<223> OTHER INFORMATION: X is S, D or A
<220> FEATURE:
<221> NAME/KEY: misc_feature
<222> LOCATION: (7)..(7)
<223> OTHER INFORMATION: X is C or Abu wherein the cysteine residue can
      be inked to the cysteine residue of X in position 9 by a disulfide
      bond
<220> FEATURE:
<221> NAME/KEY: misc_feature
<222> LOCATION: (9)..(9)
<223> OTHER INFORMATION: X is R-S, R-S-Nm, R-S-C-G, R-Abu-Nm, R-Abu-C-G,
      K-iPr-S-Nm or K-iPr-S-C-G wherein the cysteine residue can be
      linked to the cysteine residue of X in position 7 by a disulfide
      bond

<400> SEQUENCE: 1

Xaa Ser Xaa Trp Ser Xaa Xaa Ser Xaa
1               5

<210> SEQ ID NO 2
<211> LENGTH: 9
<212> TYPE: PRT
<213> ORGANISM: Artificial Sequence
<220> FEATURE:
<223> OTHER INFORMATION: Peptide compound
<220> FEATURE:
<221> NAME/KEY: MISC_FEATURE
<222> LOCATION: (1)..(1)
<223> OTHER INFORMATION: X is W or L-Nal2
<220> FEATURE:
<221> NAME/KEY: MISC_FEATURE
<222> LOCATION: (3)..(3)
<223> OTHER INFORMATION: X is G
<220> FEATURE:
<221> NAME/KEY: MISC_FEATURE
<222> LOCATION: (6)..(6)
<223> OTHER INFORMATION: X is S
<220> FEATURE:
<221> NAME/KEY: MISC_FEATURE
<222> LOCATION: (7)..(7)
<223> OTHER INFORMATION: X is C or Abu wherein the cysteine residue can
      be linked to the cysteine residue of X in position 9 by a
      disulfide bond
<220> FEATURE:
<221> NAME/KEY: MISC_FEATURE
<222> LOCATION: (9)..(9)
<223> OTHER INFORMATION: X is R-S, R-S-Nm, R-S-C-G, R-Abu-Nm, R-Abu-C-G,
      K-iPr-S-Nm or K-iPr-S-C-G wherein the cysteine residue can be
      linked to the cysteine residue of X in position 7 by a disulfide
      bond

<400> SEQUENCE: 2

Xaa Ser Xaa Trp Ser Xaa Xaa Ser Xaa
1               5

```
<210> SEQ ID NO 3
<211> LENGTH: 10
<212> TYPE: PRT
<213> ORGANISM: Artificial Sequence
<220> FEATURE:
<223> OTHER INFORMATION: Peptide compound
<220> FEATURE:
<221> NAME/KEY: misc_feature
<222> LOCATION: (7)..(7)
<223> OTHER INFORMATION: X is C or Abu

<400> SEQUENCE: 3

Trp Ser Gly Trp Ser Ser Xaa Ser Arg Ser
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Peptide compound

<400> SEQUENCE: 4

Trp Ser Gly Trp Ser Ser Cys Ser Arg Ser
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Peptide compound
<220> FEATURE:
<221> NAME/KEY: misc_feature
<222> LOCATION: (9)..(9)
<223> OTHER INFORMATION: the COOH end has been replaced by a NH2 end

<400> SEQUENCE: 5

Trp Ser Gly Trp Ser Ser Cys Ser Arg Ser
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Peptide compound

<400> SEQUENCE: 6

Trp Ser Gly Trp Ser Ser Cys Ser Arg Ser Cys Gly
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Peptide compound
<220> FEATURE:
<221> NAME/KEY: DISULFID
<222> LOCATION: (7)..(7)
<223> OTHER INFORMATION: the cysteine residue in position 7 is linked to
      the cysteine residue in position 11 by a disulfide bond
<220> FEATURE:
<221> NAME/KEY: DISULFID
<222> LOCATION: (11)..(11)
<223> OTHER INFORMATION: the cysteine residue in position 11 is linked
      to the cysteine residue in position 7 by a disulfide bond

<400> SEQUENCE: 7
```

```
Trp Ser Gly Trp Ser Ser Cys Ser Arg Ser Cys Gly
1               5                   10
```

<210> SEQ ID NO 8
<211> LENGTH: 10
<212> TYPE: PRT
<213> ORGANISM: Artificial Sequence
<220> FEATURE:
<223> OTHER INFORMATION: Peptide compound
<220> FEATURE:
<221> NAME/KEY: misc_feature
<222> LOCATION: (10)..(10)
<223> OTHER INFORMATION: X is Abu the COOH end has been replaced by a
      NH2 end

<400> SEQUENCE: 8

```
Trp Ser Gly Trp Ser Ser Cys Ser Arg Xaa
1               5                   10
```

<210> SEQ ID NO 9
<211> LENGTH: 12
<212> TYPE: PRT
<213> ORGANISM: Artificial Sequence
<220> FEATURE:
<223> OTHER INFORMATION: Peptide compound
<220> FEATURE:
<221> NAME/KEY: misc_feature
<222> LOCATION: (10)..(10)
<223> OTHER INFORMATION: X is Abu

<400> SEQUENCE: 9

```
Trp Ser Gly Trp Ser Ser Cys Ser Arg Xaa Cys Gly
1               5                   10
```

<210> SEQ ID NO 10
<211> LENGTH: 12
<212> TYPE: PRT
<213> ORGANISM: Artificial Sequence
<220> FEATURE:
<223> OTHER INFORMATION: Peptide compound
<220> FEATURE:
<221> NAME/KEY: DISULFID
<222> LOCATION: (7)..(7)
<223> OTHER INFORMATION: the cysteine residue in position 7 is linked to
      the cysteine residue in position 11 by a disulfide bond
<220> FEATURE:
<221> NAME/KEY: MISC_FEATURE
<222> LOCATION: (10)..(10)
<223> OTHER INFORMATION: X is Abu
<220> FEATURE:
<221> NAME/KEY: DISULFID
<222> LOCATION: (11)..(11)
<223> OTHER INFORMATION: the cysteine residue in position 11 is linked
      to the cysteine residue in position 7 by a disulfide bond

<400> SEQUENCE: 10

```
Trp Ser Gly Trp Ser Ser Cys Ser Arg Xaa Cys Gly
1               5                   10
```

<210> SEQ ID NO 11
<211> LENGTH: 11
<212> TYPE: PRT
<213> ORGANISM: Artificial Sequence
<220> FEATURE:
<223> OTHER INFORMATION: Peptide compound
<220> FEATURE:
<221> NAME/KEY: misc_feature
<222> LOCATION: (10)..(10)
<223> OTHER INFORMATION: X is iPr
<220> FEATURE:
<221> NAME/KEY: misc_feature
<222> LOCATION: (11)..(11)

```
<223> OTHER INFORMATION: the CCOH end has been replaced by a NH2 end

<400> SEQUENCE: 11

Trp Ser Gly Trp Ser Ser Cys Ser Lys Xaa Ser
1               5                   10

<210> SEQ ID NO 12
<211> LENGTH: 13
<212> TYPE: PRT
<213> ORGANISM: Artificial Sequence
<220> FEATURE:
<223> OTHER INFORMATION: Peptide compound
<220> FEATURE:
<221> NAME/KEY: misc_feature
<222> LOCATION: (10)..(10)
<223> OTHER INFORMATION: X is iPr

<400> SEQUENCE: 12

Trp Ser Gly Trp Ser Ser Cys Ser Lys Xaa Ser Cys Gly
1               5                   10

<210> SEQ ID NO 13
<211> LENGTH: 13
<212> TYPE: PRT
<213> ORGANISM: Artificial Sequence
<220> FEATURE:
<223> OTHER INFORMATION: Peptide compound
<220> FEATURE:
<221> NAME/KEY: DISULFID
<222> LOCATION: (7)..(7)
<223> OTHER INFORMATION: the cysteine residue in position 7 is linked to
      the cysteine residue in position 12 by a disulfide bond
<220> FEATURE:
<221> NAME/KEY: MISC_FEATURE
<222> LOCATION: (10)..(10)
<223> OTHER INFORMATION: X is iPr
<220> FEATURE:
<221> NAME/KEY: DISULFID
<222> LOCATION: (12)..(12)
<223> OTHER INFORMATION: the cysteine residue in position 12 is linked
      to the cysteine residue in position 7 by a disulfide bond

<400> SEQUENCE: 13

Trp Ser Gly Trp Ser Ser Cys Ser Lys Xaa Ser Cys Gly
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Peptide compound
<220> FEATURE:
<221> NAME/KEY: misc_feature
<222> LOCATION: (7)..(7)
<223> OTHER INFORMATION: X is Abu

<400> SEQUENCE: 14

Trp Ser Gly Trp Ser Ser Xaa Ser Arg Ser
1               5                   10

<210> SEQ ID NO 15
<211> LENGTH: 10
<212> TYPE: PRT
<213> ORGANISM: Artificial Sequence
<220> FEATURE:
<223> OTHER INFORMATION: Peptide compound
<220> FEATURE:
<221> NAME/KEY: misc_feature
<222> LOCATION: (7)..(7)
<223> OTHER INFORMATION: X is Abu
```

```
<220> FEATURE:
<221> NAME/KEY: misc_feature
<222> LOCATION: (10)..(10)
<223> OTHER INFORMATION: the COOH end has been replaced by a NH2 end

<400> SEQUENCE: 15

Trp Ser Gly Trp Ser Ser Xaa Ser Arg Ser
1               5                   10

<210> SEQ ID NO 16
<211> LENGTH: 12
<212> TYPE: PRT
<213> ORGANISM: Artificial Sequence
<220> FEATURE:
<223> OTHER INFORMATION: Peptide compound
<220> FEATURE:
<221> NAME/KEY: misc_feature
<222> LOCATION: (7)..(7)
<223> OTHER INFORMATION: X is Abu

<400> SEQUENCE: 16

Trp Ser Gly Trp Ser Ser Xaa Ser Arg Ser Cys Gly
1               5                   10

<210> SEQ ID NO 17
<211> LENGTH: 10
<212> TYPE: PRT
<213> ORGANISM: Artificial Sequence
<220> FEATURE:
<223> OTHER INFORMATION: Peptide compound
<220> FEATURE:
<221> NAME/KEY: misc_feature
<222> LOCATION: (7)..(7)
<223> OTHER INFORMATION: X is Abu
<220> FEATURE:
<221> NAME/KEY: misc_feature
<222> LOCATION: (10)..(10)
<223> OTHER INFORMATION: X is Abu the COOH end has been replaced by a
      NH2 end

<400> SEQUENCE: 17

Trp Ser Gly Trp Ser Ser Xaa Ser Arg Xaa
1               5                   10

<210> SEQ ID NO 18
<211> LENGTH: 12
<212> TYPE: PRT
<213> ORGANISM: Artificial Sequence
<220> FEATURE:
<223> OTHER INFORMATION: Peptide compound
<220> FEATURE:
<221> NAME/KEY: misc_feature
<222> LOCATION: (7)..(7)
<223> OTHER INFORMATION: X is Abu
<220> FEATURE:
<221> NAME/KEY: misc_feature
<222> LOCATION: (10)..(10)
<223> OTHER INFORMATION: X is Abu

<400> SEQUENCE: 18

Trp Ser Gly Trp Ser Ser Xaa Ser Arg Xaa Cys Gly
1               5                   10

<210> SEQ ID NO 19
<211> LENGTH: 11
<212> TYPE: PRT
<213> ORGANISM: Artificial Sequence
<220> FEATURE:
<223> OTHER INFORMATION: Peptide compound
<220> FEATURE:
<221> NAME/KEY: misc_feature
```

```
<222> LOCATION: (7)..(7)
<223> OTHER INFORMATION: X is Abu
<220> FEATURE:
<221> NAME/KEY: misc_feature
<222> LOCATION: (10)..(10)
<223> OTHER INFORMATION: X is iPr
<220> FEATURE:
<221> NAME/KEY: misc_feature
<222> LOCATION: (11)..(11)
<223> OTHER INFORMATION: the COOH end has been replaced y a NH2 end

<400> SEQUENCE: 19

Trp Ser Gly Trp Ser Ser Xaa Ser Lys Xaa Ser
1               5                   10

<210> SEQ ID NO 20
<211> LENGTH: 13
<212> TYPE: PRT
<213> ORGANISM: Artificial Sequence
<220> FEATURE:
<223> OTHER INFORMATION: Peptide compound
<220> FEATURE:
<221> NAME/KEY: misc_feature
<222> LOCATION: (7)..(7)
<223> OTHER INFORMATION: X is Abu
<220> FEATURE:
<221> NAME/KEY: misc_feature
<222> LOCATION: (10)..(10)
<223> OTHER INFORMATION: X is iPr

<400> SEQUENCE: 20

Trp Ser Gly Trp Ser Ser Xaa Ser Lys Xaa Ser Cys Gly
1               5                   10

<210> SEQ ID NO 21
<211> LENGTH: 10
<212> TYPE: PRT
<213> ORGANISM: Artificial Sequence
<220> FEATURE:
<223> OTHER INFORMATION: Peptide compound
<220> FEATURE:
<221> NAME/KEY: misc_feature
<222> LOCATION: (1)..(1)
<223> OTHER INFORMATION: X is L-Nal2

<400> SEQUENCE: 21

Xaa Ser Gly Trp Ser Ser Cys Ser Arg Ser
1               5                   10

<210> SEQ ID NO 22
<211> LENGTH: 10
<212> TYPE: PRT
<213> ORGANISM: Artificial Sequence
<220> FEATURE:
<223> OTHER INFORMATION: Peptide compound
<220> FEATURE:
<221> NAME/KEY: misc_feature
<222> LOCATION: (1)..(1)
<223> OTHER INFORMATION: X is L-Nal2
<220> FEATURE:
<221> NAME/KEY: misc_feature
<222> LOCATION: (10)..(10)
<223> OTHER INFORMATION: the COOH end has been replaced by a NH2 end

<400> SEQUENCE: 22

Xaa Ser Gly Trp Ser Ser Cys Ser Arg Ser
1               5                   10

<210> SEQ ID NO 23
<211> LENGTH: 12
<212> TYPE: PRT
```

```
<213> ORGANISM: Artificial Sequence
<220> FEATURE:
<223> OTHER INFORMATION: Peptide compound
<220> FEATURE:
<221> NAME/KEY: misc_feature
<222> LOCATION: (1)..(1)
<223> OTHER INFORMATION: X is L-Nal2

<400> SEQUENCE: 23

Xaa Ser Gly Trp Ser Ser Cys Ser Arg Ser Cys Gly
1               5                   10

<210> SEQ ID NO 24
<211> LENGTH: 12
<212> TYPE: PRT
<213> ORGANISM: Artificial Sequence
<220> FEATURE:
<223> OTHER INFORMATION: Peptide compound
<220> FEATURE:
<221> NAME/KEY: misc_feature
<222> LOCATION: (1)..(1)
<223> OTHER INFORMATION: X is L-Nal2
<220> FEATURE:
<221> NAME/KEY: DISULFID
<222> LOCATION: (7)..(7)
<223> OTHER INFORMATION: the cysteine residue in position 7 is linked to
      the cysteine residue in position 11 by a disulfide bond
<220> FEATURE:
<221> NAME/KEY: DISULFID
<222> LOCATION: (11)..(11)
<223> OTHER INFORMATION: the cysteine residue in position 11 is linked
      to the cysteine residue in position 7 by a disulfide bond

<400> SEQUENCE: 24

Xaa Ser Gly Trp Ser Ser Cys Ser Arg Ser Cys Gly
1               5                   10

<210> SEQ ID NO 25
<211> LENGTH: 10
<212> TYPE: PRT
<213> ORGANISM: Artificial Sequence
<220> FEATURE:
<223> OTHER INFORMATION: Peptide compound
<220> FEATURE:
<221> NAME/KEY: misc_feature
<222> LOCATION: (1)..(1)
<223> OTHER INFORMATION: X is L-Nal2
<220> FEATURE:
<221> NAME/KEY: misc_feature
<222> LOCATION: (10)..(10)
<223> OTHER INFORMATION: X is Abu the COOH end has been replaced by a
      NH2 end

<400> SEQUENCE: 25

Xaa Ser Gly Trp Ser Ser Cys Ser Arg Xaa
1               5                   10

<210> SEQ ID NO 26
<211> LENGTH: 12
<212> TYPE: PRT
<213> ORGANISM: Artificial Sequence
<220> FEATURE:
<223> OTHER INFORMATION: Peptide compound
<220> FEATURE:
<221> NAME/KEY: misc_feature
<222> LOCATION: (1)..(1)
<223> OTHER INFORMATION: X is L-Nal2
<220> FEATURE:
<221> NAME/KEY: misc_feature
<222> LOCATION: (10)..(10)
<223> OTHER INFORMATION: X is Abu

<400> SEQUENCE: 26
```

```
Xaa Ser Gly Trp Ser Ser Cys Ser Arg Xaa Cys Gly
1               5                   10
```

<210> SEQ ID NO 27
<211> LENGTH: 12
<212> TYPE: PRT
<213> ORGANISM: Artificial Sequence
<220> FEATURE:
<223> OTHER INFORMATION: Peptide compound
<220> FEATURE:
<221> NAME/KEY: misc_feature
<222> LOCATION: (1)..(1)
<223> OTHER INFORMATION: X is L-Nal2
<220> FEATURE:
<221> NAME/KEY: DISULFID
<222> LOCATION: (7)..(7)
<223> OTHER INFORMATION: the cysteine residue in position 7 is linked to
      the cysteine residue in position 11 by a disulfide bond
<220> FEATURE:
<221> NAME/KEY: MISC_FEATURE
<222> LOCATION: (10)..(10)
<223> OTHER INFORMATION: X is Abu
<220> FEATURE:
<221> NAME/KEY: DISULFID
<222> LOCATION: (11)..(11)
<223> OTHER INFORMATION: the cysteine residue in position 11 is linked
      to the cysteine residue in position 7 by a disulfide bond

<400> SEQUENCE: 27

```
Xaa Ser Gly Trp Ser Ser Cys Ser Arg Xaa Cys Gly
1               5                   10
```

<210> SEQ ID NO 28
<211> LENGTH: 11
<212> TYPE: PRT
<213> ORGANISM: Artificial Sequence
<220> FEATURE:
<223> OTHER INFORMATION: Peptide compound
<220> FEATURE:
<221> NAME/KEY: misc_feature
<222> LOCATION: (1)..(1)
<223> OTHER INFORMATION: X is L-Nal2
<220> FEATURE:
<221> NAME/KEY: misc_feature
<222> LOCATION: (10)..(10)
<223> OTHER INFORMATION: X is iPr
<220> FEATURE:
<221> NAME/KEY: misc_feature
<222> LOCATION: (11)..(11)
<223> OTHER INFORMATION: the COOH end has been replaced by a NH2 end

<400> SEQUENCE: 28

```
Xaa Ser Gly Trp Ser Ser Cys Ser Lys Xaa Ser
1               5                   10
```

<210> SEQ ID NO 29
<211> LENGTH: 13
<212> TYPE: PRT
<213> ORGANISM: Artificial Sequence
<220> FEATURE:
<223> OTHER INFORMATION: Peptide compound
<220> FEATURE:
<221> NAME/KEY: misc_feature
<222> LOCATION: (1)..(1)
<223> OTHER INFORMATION: X is L-Nal2
<220> FEATURE:
<221> NAME/KEY: misc_feature
<222> LOCATION: (10)..(10)
<223> OTHER INFORMATION: X is iPr

<400> SEQUENCE: 29

```
Xaa Ser Gly Trp Ser Ser Cys Ser Lys Xaa Ser Cys Gly
```

```
1               5                   10
```

```
<210> SEQ ID NO 30
<211> LENGTH: 13
<212> TYPE: PRT
<213> ORGANISM: Artificial Sequence
<220> FEATURE:
<223> OTHER INFORMATION: Peptide compound
<220> FEATURE:
<221> NAME/KEY: misc_feature
<222> LOCATION: (1)..(1)
<223> OTHER INFORMATION: X is L-Nal2
<220> FEATURE:
<221> NAME/KEY: DISULFID
<222> LOCATION: (7)..(7)
<223> OTHER INFORMATION: the cysteine residue in position 7 is linked to
      the cysteine residue in position 12 by a disulfide bond
<220> FEATURE:
<221> NAME/KEY: misc_feature
<222> LOCATION: (10)..(10)
<223> OTHER INFORMATION: X is iPr
<220> FEATURE:
<221> NAME/KEY: DISULFID
<222> LOCATION: (12)..(12)
<223> OTHER INFORMATION: the cysteine residue in position 12 is linked
      to the cysteine residue in position 7 by a disulfide bond

<400> SEQUENCE: 30

Xaa Ser Gly Trp Ser Ser Cys Ser Lys Xaa Ser Cys Gly
1               5                   10

<210> SEQ ID NO 31
<211> LENGTH: 10
<212> TYPE: PRT
<213> ORGANISM: Artificial Sequence
<220> FEATURE:
<223> OTHER INFORMATION: Peptide compound
<220> FEATURE:
<221> NAME/KEY: misc_feature
<222> LOCATION: (1)..(1)
<223> OTHER INFORMATION: X is L-Nal2
<220> FEATURE:
<221> NAME/KEY: misc_feature
<222> LOCATION: (7)..(7)
<223> OTHER INFORMATION: X is Abu

<400> SEQUENCE: 31

Xaa Ser Gly Trp Ser Ser Xaa Ser Arg Ser
1               5                   10

<210> SEQ ID NO 32
<211> LENGTH: 10
<212> TYPE: PRT
<213> ORGANISM: Artificial Sequence
<220> FEATURE:
<223> OTHER INFORMATION: Peptide compound
<220> FEATURE:
<221> NAME/KEY: misc_feature
<222> LOCATION: (1)..(1)
<223> OTHER INFORMATION: X is L-Nal2
<220> FEATURE:
<221> NAME/KEY: misc_feature
<222> LOCATION: (7)..(7)
<223> OTHER INFORMATION: X is Abu
<220> FEATURE:
<221> NAME/KEY: misc_feature
<222> LOCATION: (10)..(10)
<223> OTHER INFORMATION: the COOH end has been replaced by a NH2 end

<400> SEQUENCE: 32

Xaa Ser Gly Trp Ser Ser Xaa Ser Arg Ser
1               5                   10
```

```
<210> SEQ ID NO 33
<211> LENGTH: 12
<212> TYPE: PRT
<213> ORGANISM: Artificial Sequence
<220> FEATURE:
<223> OTHER INFORMATION: Peptide compound
<220> FEATURE:
<221> NAME/KEY: misc_feature
<222> LOCATION: (1)..(1)
<223> OTHER INFORMATION: X is L-Nal2
<220> FEATURE:
<221> NAME/KEY: misc_feature
<222> LOCATION: (7)..(7)
<223> OTHER INFORMATION: X is Abu

<400> SEQUENCE: 33

Xaa Ser Gly Trp Ser Ser Xaa Ser Arg Ser Cys Gly
1               5                   10

<210> SEQ ID NO 34
<211> LENGTH: 10
<212> TYPE: PRT
<213> ORGANISM: Artificial Sequence
<220> FEATURE:
<223> OTHER INFORMATION: Peptide compound
<220> FEATURE:
<221> NAME/KEY: misc_feature
<222> LOCATION: (1)..(1)
<223> OTHER INFORMATION: X is L-Nal2
<220> FEATURE:
<221> NAME/KEY: misc_feature
<222> LOCATION: (7)..(7)
<223> OTHER INFORMATION: X is Abu
<220> FEATURE:
<221> NAME/KEY: misc_feature
<222> LOCATION: (10)..(10)
<223> OTHER INFORMATION: X is Abu the COOH end has been replaced by a
      NH2 end

<400> SEQUENCE: 34

Xaa Ser Gly Trp Ser Ser Xaa Ser Arg Xaa
1               5                   10

<210> SEQ ID NO 35
<211> LENGTH: 12
<212> TYPE: PRT
<213> ORGANISM: Artificial Sequence
<220> FEATURE:
<223> OTHER INFORMATION: Peptide compound
<220> FEATURE:
<221> NAME/KEY: misc_feature
<222> LOCATION: (1)..(1)
<223> OTHER INFORMATION: X is L-Nal2
<220> FEATURE:
<221> NAME/KEY: misc_feature
<222> LOCATION: (7)..(7)
<223> OTHER INFORMATION: X is Abu
<220> FEATURE:
<221> NAME/KEY: misc_feature
<222> LOCATION: (10)..(10)
<223> OTHER INFORMATION: X is Abu

<400> SEQUENCE: 35

Xaa Ser Gly Trp Ser Ser Xaa Ser Arg Xaa Cys Gly
1               5                   10

<210> SEQ ID NO 36
<211> LENGTH: 11
<212> TYPE: PRT
<213> ORGANISM: Artificial Sequence
<220> FEATURE:
<223> OTHER INFORMATION: Peptide compound
```

```
<220> FEATURE:
<221> NAME/KEY: misc_feature
<222> LOCATION: (1)..(1)
<223> OTHER INFORMATION: X is L-Nal2
<220> FEATURE:
<221> NAME/KEY: misc_feature
<222> LOCATION: (7)..(7)
<223> OTHER INFORMATION: X is Abu
<220> FEATURE:
<221> NAME/KEY: misc_feature
<222> LOCATION: (10)..(10)
<223> OTHER INFORMATION: X is iPr
<220> FEATURE:
<221> NAME/KEY: misc_feature
<222> LOCATION: (11)..(11)
<223> OTHER INFORMATION: the COOH end has been replaced a NH2 end

<400> SEQUENCE: 36

Xaa Ser Gly Trp Ser Ser Xaa Ser Lys Xaa Ser
1               5                   10

<210> SEQ ID NO 37
<211> LENGTH: 13
<212> TYPE: PRT
<213> ORGANISM: Artificial Sequence
<220> FEATURE:
<223> OTHER INFORMATION: Peptide compound
<220> FEATURE:
<221> NAME/KEY: misc_feature
<222> LOCATION: (1)..(1)
<223> OTHER INFORMATION: X is L-Nal2
<220> FEATURE:
<221> NAME/KEY: misc_feature
<222> LOCATION: (7)..(7)
<223> OTHER INFORMATION: X is Abu
<220> FEATURE:
<221> NAME/KEY: misc_feature
<222> LOCATION: (10)..(10)
<223> OTHER INFORMATION: X is iPr

<400> SEQUENCE: 37

Xaa Ser Gly Trp Ser Ser Xaa Ser Lys Xaa Ser Cys Gly
1               5                   10
```